United States Patent [19]

Kunze

[11] Patent Number: 4,590,789

[45] Date of Patent: May 27, 1986

[54] REMOTE CALIBRATOR

[76] Inventor: Manfred C. Kunze, 8401 Tradewind Cr., Huntington Beach, Calif. 92646

[21] Appl. No.: 646,634

[22] Filed: Aug. 31, 1984

[51] Int. Cl.⁴ ............................................. G01C 25/00
[52] U.S. Cl. .................................. 73/1 G; 73/864.81
[58] Field of Search ............................ 73/1 G, 864.81

[56] References Cited

U.S. PATENT DOCUMENTS

| | | | |
|---|---|---|---|
| 3,421,362 | 4/1965 | Schaeffer | 73/23 |
| 3,729,979 | 5/1973 | Wilberg et al. | 73/1 R |
| 4,177,667 | 12/1979 | Rolf et al. | 73/1 G |
| 4,205,550 | 6/1980 | Swanson | 73/1 G |
| 4,279,142 | 7/1981 | McIntyre | 73/1 B |
| 4,489,590 | 12/1984 | Hadden | 73/1 G |

OTHER PUBLICATIONS

Data Sheet for Model RC-1 Remote Calibrator, dated Jan., 1982, for General Monitors, Inc.
General Monitors, Inc. "United States Price List-Remote Calibration RC-1 System, Effective Mar. 31, 1982".

Primary Examiner—Jerry W. Myracle
Attorney, Agent, or Firm—Roberts and Quiogue

[57] ABSTRACT

An improved remote calibration is disclosed for calibrating a gas sensing device. A housing is provided which receives the gas sensor in an open end and a valve/diaphragm assembly in a receiving end. A plurality of openings are formed in the housing adjacent the open end to allow the ambient gas to communicate with the gas sensor. A cap is provided to define a gas chamber between the cap and the rolling diaphragm. The valve is carried by the diaphragm. A gas inlet in the cap admits pressurized gas, driving the diaphragm and the valve toward the open end of the housing to obstruct the ambient gas from the gas sensing device. An orifice is provided in the diaphragm and communicates with a bore in the valve. Calibration gas passes through the orifice and the bore in the valve and floods the region around the gas sensor.

25 Claims, 4 Drawing Figures

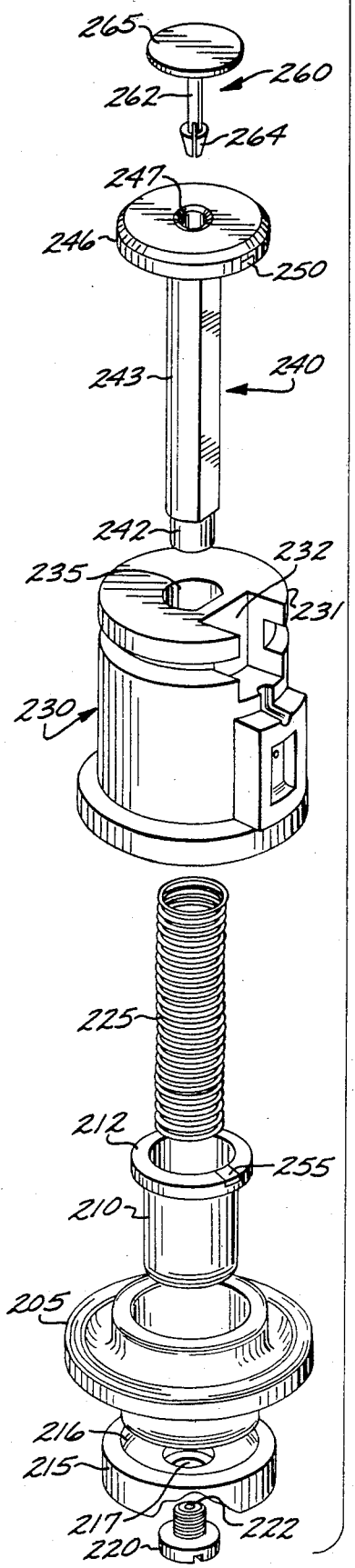
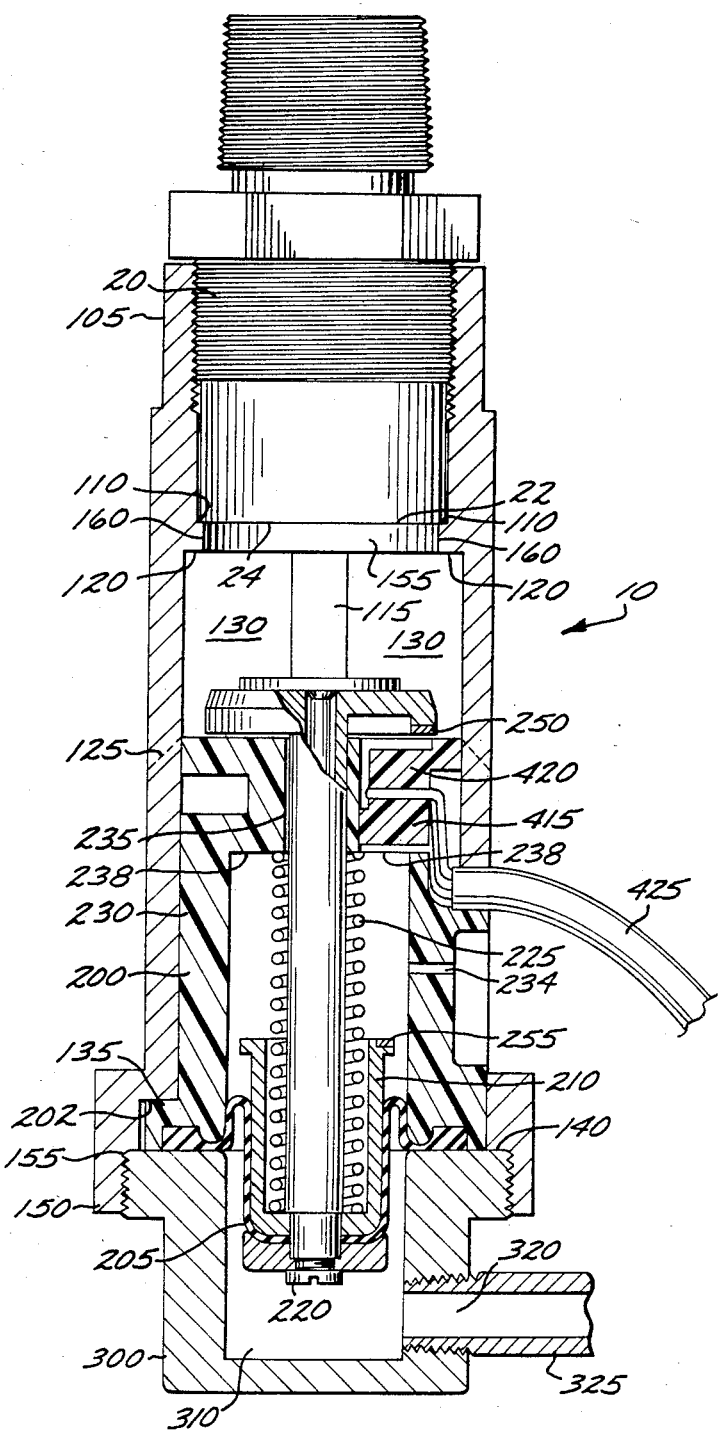

REMOTE CALIBRATOR

BACKGROUND OF THE INVENTION

Various gas sensing devices are known which are relatively small and rugged and which are thus well suited for permanent installation in locations that are not easily accessible. Such devices include, for example, the series 10000-1 hydrocarbon sensors manufactured and sold by General Monitors, Inc., of Costa Mesa, Calif. These devices are often referred to as catalytic devices and can be typically mounted near or on the ceilings of rooms or mine shafts or inside ducts or flues, where access is difficult and in some instances dangerous. These devices provide signals that can be applied to suitable instruments located, for example, in a remote control room. The instruments display readings or indications of the gas concentrations detected by the gas sensing devices.

It is desirable to calibrate each such gas sensing device periodically to ensure that the data provided by the devices is accurate. In the past, the calibration has required that a worker carry a source of calibration gas such as a high-pressure tank or bottle to the sensing device. With a device such as one of th hydrocarbon sensing devices described above, the worker would first cover the device so that any hydrocarbon gas within the sensor would be consumed by the sensor, thereby allowing the sensor to be zeroed or calibrated with respect to an absence of hydrocarbon gas. Once this is done, the worker would then expose the sensor to calibration gas. The reading or indication provided by the sensor would then be calibrated with respect to the known concentration of the calibration gas.

As can be appreciated, this calibration process requires a worker to perform calibration operations at the sensing device itself. Where the device is not easily accessible, the calibration process becomes difficult and can expose the worker to dangerous environments. Moreover, the worker may be required to perform various manual tasks such as manipulating a tank of calibration gas at the sensing device while positioned on a ladder, further increasing the difficulty of the calibration task and also increasing the worker's exposure to hazardous working conditions. Because of the difficulty associated with performing the calibration process, gas sensing devices may not be calibrated as often as desirable, leading to inaccuracies and unreliable data from the gas monitoring system.

A remote calibrator device is described in application Ser. No. 314,363, entitled "Remote Calibrator, filed in the U.S. Patent and Trademark Office on Oct. 23, 1981 now abandoned (presently understood to be in an abandoned state). The calibrator device described in that application, which was assigned to the same assignee as the present application, was relatively expensive to manufacture and maintain, and subject to gas leakage over the wide temperature range within which the sensor and calibrator are expected to operate.

Thus, there is a need for a device which can be reliably used to remotely calibrate gas sensing devices with a minimum of worker time and without exposing the worker to dangerous environments or working conditions.

SUMMARY OF THE INVENTION

An exemplary remote calibrator in accordance with the present invention overcomes the limitations and difficulties set forth above. Such a remote calibrator is located at the gas sensing device itself and can be operated from a remote position that is easily accessible. Several remote calibrators can be operated by a single worker from the same remote position to further increase productivity. The ease and simplicity of operation of the remote calibrator encourages frequent calibration of the gas sensing devices to better ensure accuracy of the gas sensing system.

A remote calibrator as disclosed herein includes a housing with an open end and a receiving end for receiving the gas sensor, the housing having a plurality of openings formed therein adjacent the receiving end for communicating ambient gas to the sensing port of the sensor.

A movable valve member is disposed into the open end of the housing and is carried by a diaphragm assembly. A cap member closes the receiving end of the housing, the diaphragm and cap member defining a gas chamber. An orifice is provided in the diaphragm and a passageway is formed through the valve in communication with the orifice.

The diaphragm and valve are biased to a normally open position with the valve head toward the open end. In this position, the openings in the housing allow ambient gas to freely pass through the housing walls and reach a gas sensing port of the sensing device.

The gas chamber is adapted to receive calibration gas under pressure. The pressure drives the diaphragm and the valve toward the receiving end of the housing and the gas sensor. The valve head is inserted in a closed position into an opening in the housing to define a second gas chamber at the sensing port of the gas sensor, thereby isolating the port from the ambient environment. Calibration gas flows through the orifice and valve passageway to flood the sensing port with calibration gas. The calibration gas is exhausted from the second gas chamber through an opening between the valve head and the housing.

Once calibration is completed the flow of calibration gas is shut off, the diaphragm withdraws to its rest position and the valve returns to the open end of the housing, again allowing ambient gas to circulate to the sensing device port. The calibration gas can be applied to the remote calibrator conveniently via a tube which is terminated at a location which is easily accessible. Thus, there is no need for a worker to gain access to the sensing device itself but instead need only connect a calibration gas source to the tube leading to the remote calibrator.

Thus, a remote calibrator as contemplated by the present invention saves time and increased worker productivity. Furthermore, the worker need not be exposed to dangerous environments or working conditions in order to calibrate a gas sensing device. The remote calibrator is simple, reliable and can be manufactured employing techniques such as injection molding.

It is thus an object of the present invention to provide a rugged, remote calibrator for gas sensing devices, which is capable of reliable operation over a wide temperature range.

It is a further object of the present invention to provide a remote calibrator which operates to cover the gas sensing device port in response to gas pressure and which disperses calibration gas around the sensing port.

It is another object of the present invention to provide a remote calibrator of simple design.

BRIEF DESCRIPTION OF THE DRAWINGS

These and other features and advantages of the present invention will become more apparent from the following detailed description of an exemplary embodiment thereof, as illustrated in the accompanying drawings, in which:

FIG. 1 is a cross-sectional, partially broken-away view of the preferred embodiment of the invention.

FIG. 2 is an exploded view of the valve and diaphragm assembly of the preferred embodiment.

DETAILED DESCRIPTION OF THE PREFERRED EMBODIMENT

The present invention comprises a novel improved remote calibrator. The following description is presented to enable any person skilled in the art to make and use the invention, and is provided in the context of a particular application and its requirements. Various modifications to the preferred embodiment will be readily apparent to those skilled in the art, and the generic principles defined herein may be applied to other embodiments and applications. Thus, the present invention is not intended to be limited to the embodiment shown, but is to be accorded the widest scope consistent with the principles and novel features disclosed herein.

Figure 3:
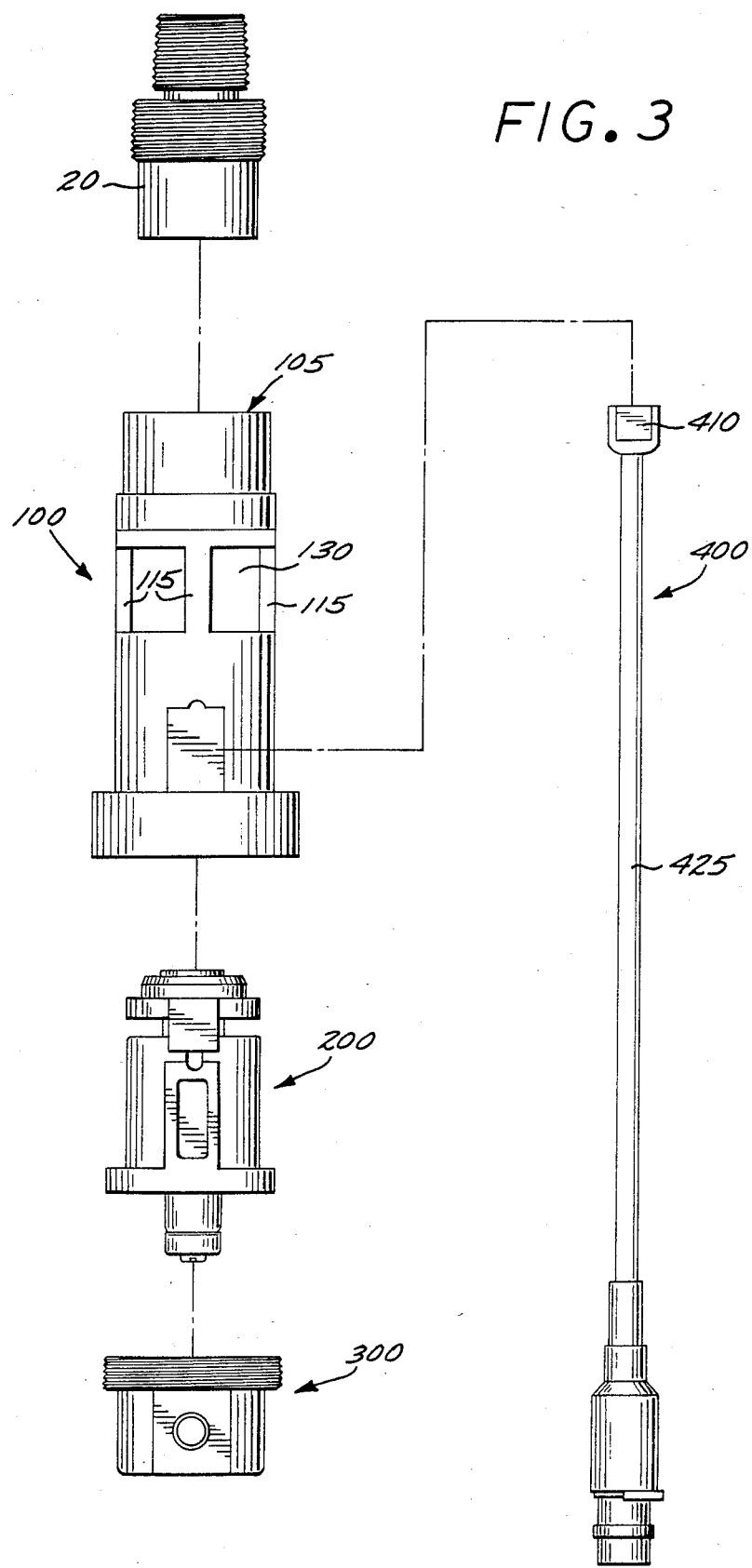
FIG. 3 is an exploded view illustrating the mating relationship of the sensor housing, the valve and diaphragm assembly, the cap and sensor cable assembly of the preferred embodiment.

Referring now to FIG. 3, a remote calibrator 10 in accordance with the invention is disclosed in a partial exploded view. The calibrator 10 comprises housing 100, valve/diaphragm assembly 200, cap member 300 and valve position sensing assembly 400.

The calibrator 10 is illustrated in an assembled form in the cross-sectional view of FIG. 1. Housing 100 is a generally cylindrically hollow member having a receiving end 105 adapted to threadingly receive a suitable gas sensing device 20 such as one of the catalytic hydrocarbon sensors described above. The device 20 includes a port 24 open to the gas to be sensed by the device 20.

The end 22 of sensor 20 seats against shoulder 110 formed in housing 100. The region of the housing adjacent port 24 is defined by a plurality of ribs 115 extending from adjacent shoulder 120 to the region indicated by phantom line 125. Between the ribs 115 are a plurality of openings 130 through the wall of the sensor housing 100. These openings allow ambient gas surrounding the remote calibrator 10 to reach the port 24 and to thus be detected by the sensing device 20.

As shown in FIG. 3, the remote calibrator 10 further comprises assembly 200 and body member 300. Assembly 200 is disposed within the housing 100. As seen in FIG. 1, assembly 200 is registered in position in housing 100 by shoulders 135,140 respectively formed in housing 100 adjacent end 150. As shown in FIGS. 1 and 3, the body of housing 100 is opened out to a wider diameter, thereby defining shoulders 135,140. Matching shoulder 202 of the assembly 200 seats against shoulder 135 of the housing to register assembly 200 in position within the housing 100. It is noted that the respective shoulder pairs 135,205 and 140,210 are not mirror images, so as to key the rotational as well as the axial position of the assembly in relation to the housing.

Cap member 300 is threadingly received within end 150 of housing 100. The threaded end of the cap 300 seats against shoulder 155 formed in housing 100. Cap 300 secures the assembly 200 in position within housing 100. A gas inlet 320 is formed in the side of body 300 to allow communication between the gas chamber 310 defined within body 300 and a source of calibration gas. A tubing 325 connects the chamber 310 to a source of calibration gas.

Referring now to FIG. 2, the assembly 200 is shown in exploded view. The assembly includes rolling diaphragm 205. A modified long-stroke-rolling diaphragm, part number BFA 20/15-20, marketed by the Carl Freudenberg Company, is used as diaphragm 205 in the preferred embodiment. Other diaphragms could, of course, be used.

A diaphragm cup member 210 fits into the inner cupped region of the diaphragm 205. Orifice plate 215 is fitted to the adjacent outer surface of the diaphragm 205 and comprises an inner concave curved surface 216 adapted to mate with the adjacent end region of the diaphragm. Threaded orifice member 220 fits through bore 217 and is threadingly received in the end 242 of valve member 240. Orifice member 220 is provided with a calibrated orifice 222, which is 0.006 inches in diameter in the preferred embodiment.

Assembly 200 further comprises compression spring 225 and substantially cylindrical body 230. A circumferential slot 232 is defined in the body 230 adjacent end 231. As shown in FIGS. 1 and 3, position sensing unit 410 is received in slot 232. An opening 235 is formed in body member 230, for receiving valve member 240 therethrough. The valve 240 includes stem 243 and head portion 246. The stem is provided with a bore 247 extending from end 242 to adjacent head 246, where the diameter is reduced to define a narrowed bore and shoulder (not shown).

A vent opening 234 is formed in body 230. The end of the bore 247 adjacent end 242 is threaded to engage orifice member 220. It is noted that opening 235 in body 230, stem 243, and the opening in the diaphragm cup are correspondingly flat-sided so as to key the rotational location of the valve in position.

Permanent magnet 250 is mounted in the head 246 as shown in FIGS. 1 and 2, for example, by an adhesive. Similarly, permanent magnet 255 is mounted in the lip of diaphragm cup 210. The magnets 250,255 are oriented so that their respective south poles face each other.

As shown in FIG. 2, the stem 262 of gas deflector member 260 is fitted through bore 247. Barbs 264 at the end of stem 262 expand upon passing into enlarged bore 247 and secure the deflector in sliding relationship in valve 240. It is noted that the stem 262 is longer than the extent of the narrowed portion of bore 247 within valve 240, thereby permitting limited sliding movement of deflector 260. The reduced diameter of bore 247 is larger than that of stem 262 to permit ready flow of gas from the orifice through bore 247 around stem 262, where the gas flow is deflected by disc 265 of the deflector member.

The various elements of the assembly 200 are secured in the assembled position (shown in FIG. 1) by the threading engagement of orifice member 220 in end 242 of valve 240. Thus, compression spring 225 biases valve 240 so that the head 246 abuts end 231 of the body 230. The assembly is adapted to allow the valve to slide within opening 235 of the body from its nominal open position shown in FIG. 1 to a closed position wherein the valve has traveled against the bias force of the spring such that the lip 212 of diaphragm cup abuts the inner shoulder 238 formed within body 230.

When assembly 200 is in the assembled state, the orifice 222 communicates with bore 247. The calibrated orifice 222 provides a predetermined orifice size, 0.006 inches in the disclosed embodiment, which in turn determines the flow rate of calibration gas from gas chamber 310 through the valve bore 247.

The remote calibrator 10 includes sensor means adapted to provide visual indications at a remote location of the location of the valve, i.e., with the valve in the open position illustrated in FIG. 1, the extended, closed position, or an intermediate status. Two Hall effect sensor switch devices are employed to sense the closed and the open valve position status. The two sensor switches 415,420 are carried in rectangular module 410 attached at one end of four wire cable 425. The other end of the cable is terminated in a circular connector for ready coupling to a calibrator circuit cable. The calibration circuit provides the operator of the remote calibrator with visual indications of the valve position.

Switch module 410 is received in housing 230 as shown in FIG. 1. The cable 425 extends through an opening formed in housing 100. When switch module 410 is in place, Hall effect sensing switch 420 is disposed for sensing the magnetic field of magnet 250 when the valve is in the open position with magnet 250 adjacent switch 420. Switch 415 is disposed for sensing the magnetic field of magnet 255 when the valve is in the closed position with magnet 255 adjacent switch 415.

Figure 4:
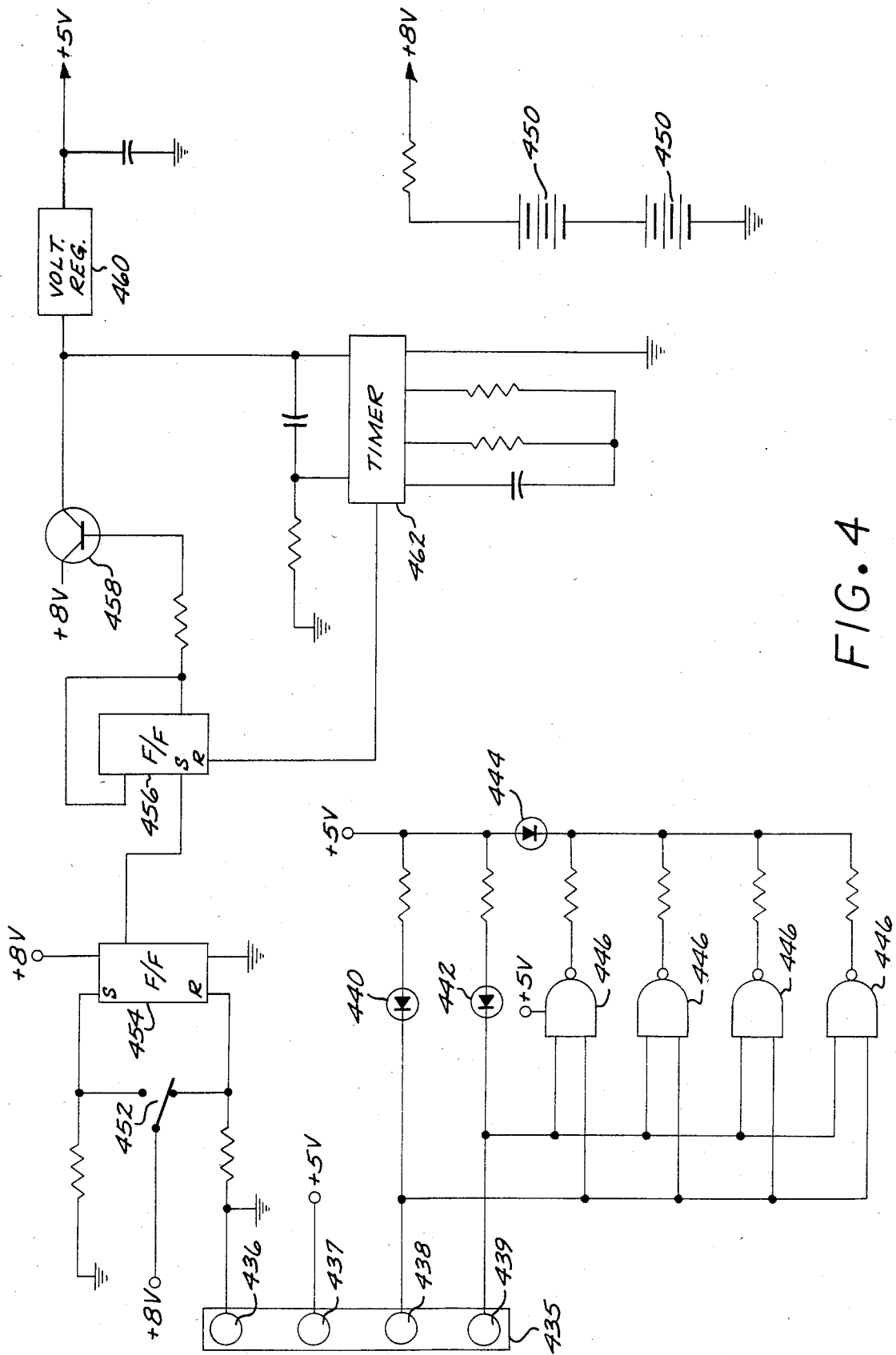
FIG. 4 is a schematic diagram of the electrical circuit employed with the valve position sensors in the preferred embodiment.

Referring now to FIG. 4, the indicator circuit schematic is disclosed. The four conductors of cable 425 are coupled to the indicator circuit via terminal board 435. The indicator circuit can be housed in a small control box at the remote location, e.g., adjacent controls for the calibration gas source, to provide the operator of the remote calibrator 10 a convenient means for monitoring the operation of the calibrator.

The Hall effect sensor devices 415,420 are Hall Effect position sensors, model 8SS3, marketed by the Micro Switch division of Honeywell Corporation. When a magnet is adjacent the sensor, the magnetic field causes the switch to conduct; the switch is open in the absence of the magnetic field.

The sensor switches are coupled to terminal board 435 via cable 425. Terminal 436 is a ground termination, while terminal 437 is coupled to a switched +5 volt supply. Terminal 438 is coupled to switch 415, which closes when the valve is in the extended, closed position. Terminal 439 is coupled to the switch 420, which closes when the valve is in the retracted, open position. Thus, when switch 415 closes, terminal 438 is grounded and green LED 440 is biased to the illuminating state, indicating the valve is in the closed, extended state for calibration. When switch 420 closes, terminal 439 is grounded, biasing green LED 442 to the illuminating state, indicating the valve is in the open, retracted position. With neither switch 415,420 closed, the outputs of NAND gates 446 are in the low state, so that red LED 444 is biased to the illuminating state when the switched +5 V supply is active. This condition indicates that the valve is disposed between the open and closed position. Four NAND gates are employed simply to ensure that the red LED is biased on.

The circuit is powered by a pair of 3.5 volt battery cells 450 to provide a non-regulated supply voltage. A single-pole, double throw push-button switch 452 is provided to activate the regulated voltage supply, by setting flip-flops 454, 456 to turn on transistor 458. Counter 462 is adapted to provide a time-out signal about eight minutes after the switch 452 activates the circuit. The time-out signal resets flip-flop 456 to turn off the transistor 458. The timer conserves the battery power in the event the operator neglects to switch the circuit off after use.

It is to be recognized that the circuitry of FIG. 4 is exemplary only and that other suitable means for indicating the position of the valve are possible.

The operation of the remote calibrator 10 will now be considered. With no calibration gas pressure applied to the remote calibrator 10 through the tubing coupled to gas inlet 320, the spring 225 biases the diaphragm 205 to the position shown. Since the valve is coupled to the diaphragm, it is carried to the open position. With the valve so oriented, the ambient gas surrounding the remote calibrator 10 freely passes through the openings 130 to the port 24 of the gas sensing device 20. As is well known to those skilled in the art, the device 20 responds to the ambient gas to provide a signal indicative of the concentration of a preselected gas within the ambient gas. It will further be understood that the remote calibrator is mounted vertically with the device 20 at the top to direct the port 24 downwardly to prevent the accumulation of water and dirt therein.

Once it is desired to calibrate the device 20, a source of calibration gas is connected to the remote end (not shown) of the tubing coupled to the gas inlet. This calibration gas may be supplied to the remote calibrator at a suitable pressure such as approximately in the range of five to twenty pounds per square inch gauge. The calibration gas pressurizes the chamber 310 and the diaphragm acts against the bias provided by the spring 225. The spring force is selected such that this calibration gas pressure is sufficient to overcome the spring bias, thus driving the diaphragm toward the gas sensing device 20. The diaphragm offers very little frictional resistance to the rolling movement of the diaphragm, a distinct improvement over frictional piston seal arrangements. The movement of the diaphragm is stopped when the lip 212 of the diaphragm cup 210 contacts shoulder 238 of the body 230. In this position the head of the valve 240 is inserted into the opening defined by ridge 160 in the housing 200 adjacent the port 24, so as to define a second gas chamber 155 adjacent the port of the sensing device. The diameters of this opening is slightly larger than the diameter of the head 246 of the valve 240, thereby allowing calibration gas to pass between the head 246 and ridge 160 when the valve is closed. The length of the valve 240 is selected so that the head does not contact the sensor 20, leaving room for extension of the gas deflector 260. The continued pressure of the calibration gas holds the diaphragm is this extended position.

The calibration gas also flows through the calibrated orifice 222 and bore 247. The orifice 222 is selected such that the calibration gas pressure causes about 0.6 cubic feet per hour of the calibration gas to flow therethrough. This flow of calibration gas passes through bore 247, forcing the deflector 260 away from head 246 of the valve. The gas floods around the deflector disc 265, providing a more uniform gas distribution within the gas chamber 155. The deflector provides more accurate calibration of the sensor. The sensor 20 typically has active and passive catalytic beads. If the calibration gas flow were directed, for example, at the active bead, one bead can be cooled more than the other, thereby providing an inaccurate reading. The deflector disperses the gas and also protects against dirt and moisture from entering bore 247. The flow of calibration gas floods the chamber 155 and thus the gas sensing device 20 with calibration gas. The calibration gas then passes through the opening between head 246 and ridges 160.

Several calibration gases may be applied to the remote calibrator in succession. For example, a first calibration gas may be a standard of zero gas which will provide a zero calibration point for the device 20, that is, the zero gas being free of the gas to which the device 20 responds. Next, a second calibration gas can be applied to the remote calibrator 10, this second calibration gas containing a predetermined concentration of the gas to which the device 20 responds. Thus, a second calibration point for the device 20 can be determined. It is to be recognized that the various calibration gases are applied to the remote calibrator 10 and, thus, the device 20 for a length of time sufficient for the device to fully respond thereto.

Once calibration of the device 20 is completed, calibration gas pressure is removed from the remote calibrator 10. The spring 225 returns the diaphragm 205 to the retracted position shown in FIG. 1, carrying valve 240 to its normally open position. When so retracted, the device 20 again senses ambient gas as described previously.

Thus, a remote calibrator in accordance with the present invention allows calibration of a gas sensing device in a location that is not readily accessible. The remote calibrator diaphragm and valve is operated by the gas pressure of the calibration gas itself, thus requiring no external power source or control facilities. The use of low pressure calibration gas to both cover the gas sensing device port and to flush the gas sensing device allows relatively simple gas tubing to be used, further decreasing the overall cost and complexity of a calibration system using the present invention.

The improved remote calibrator is adapted for inexpensive manufacture. The sensor housing 100, cap 300 and body members 230 and 210, valve 240 and deflector 260 may be fabricated using low cost injection molding techniques. There are no close, critical tolerance requirements for these parts, which not only reduce the fabrication cost but improve the reliability of the remote calibrator. The use of the rolling diaphragm solves several problems in the earlier remote calibrator device referenced above. The diaphragm offers little frictional resistance to its movement and ensures a lasting gas seal which preserves the integrity of chamber 310 against undesirable gas leaks when operation occurs over a wide temperature range. The low resistance against diaphragm movement prevents the valve from sticking in a particular position as the ambient temperature deviates from a nominal valve. The remote calibrator described herein is expected to operate reliably over the temperature range from −30° C. to +60° C. The use of the solid state Hall effect sensing switches results in extremely reliable sensor operation even in the presence of vibration and temperature extremes. Moreover, the configuration of the disclosed remote calibrator is simple to assemble and disassemble, allowing ready maintenance if required.

Having thus described one embodiment of the present invention, it is to be understood that various alternatives and modifications will be apparent to one of ordinary skill in the art given the teachings herein, and that the exemplary embodiments set forth herein shall not serve as a limitation of the scope of the appended claims.

What is claimed is:

1. A remote calibrator device for a gas sensing device wherein the sensing device includes a port for communication with the gas to be sensed, comprising:
    housing means having a receiving end for communication with the port of the gas sensing device and an open end, said housing means having openings formed therein proximate said receiving end for communicating ambient gas to said gas sensing port;
    means for providing a calibration gas chamber, said means comprising a flexible diaphragm responsive to the gas pressure in the chamber so as to move from an initial position toward the receiving end of the housing as the pressure increases;
    a movable valve member coupled to the diaphragm and arranged to extend into said open end of the housing, said valve member adapted for movement from said initial position toward said receiving end to substantially obstruct the communication of ambient gas with the port of the gas sensing device when in an extended position;
    a spring member cooperatively arranged with said diaphragm and said valve member for biasing said diaphragm and said valve to said initial position;
    a body member for supporting said diaphragm means and said valve member, said body member including means for constraining the movement of said valve along an axis extending toward the port of the gas sensing device;
    gas inlet means for communicating calibration gas into the gas chamber; and
    means for conducting the calibration gas from the gas chamber through said valve member to the port of the gas sensing device when the valve is in the extended position.

2. The invention of claim 1 wherein said valve and said diaphragm means are cooperatively arranged with the housing means so that, when the gas pressure in the gas chamber does not exceed the ambient pressure, the valve means is disposed so that the openings in the housing means are not obstructed.

3. The invention of claim 1 wherein said valve member comprises a valve stem and a valve head, the valve stem extending through an opening in said body member, and the means for conducting the calibration gas comprises a calibrated orifice provided through the diaphragm in communication with a bore in the valve.

4. The invention of claim 1 futher comprising position sensing means for providing an indication of the location of the valve member.

5. The invention of claim 4 wherein the position sensing means comprises Hall effect switches.

6. The invention of claim 1 wherein said means for providing a calibration gas chamber further comprises a cap member for sealing said open end of said housing means, said gas chamber being defined by said diaphragm and an interior region of said cap member.

7. The invention of claim 1 wherein said diaphragm comprises a circumferential lip and said cap member is threadingly received within said open end of said housing member to sandwich said circumferential lip between adjacent regions of said cap member and said body member.

8. The invention of claim 1 further comprising travel limiting means for limiting the extent of said extended position of said valve member.

9. The invention of claim 8 wherein said valve comprises a valve stem and a valve head, the valve stem extending through an opening in said body member, and wherein said travel limiting means comprises an elongated diaphragm cup member fitted adjacent said diaphragm member and having a circumferential lip region, said cup receiving one end of said spring member, and the longitudinal extent of said cup member being selected so that said lip region contacts said body member to define said extended position of said valve member.

10. The invention of claim 9 further comprising position sensing means for providing an indication of the location of the valve member, said means comprising first permanent magnet means affixed to said lip region of said cup member and a corresponding Hall effect sensor mounted to said body member so that said sensor is triggered by said first magnet when said valve member is at said extended position.

11. The invention of claim 10 wherein said valve head abuts an end of said body member when said diaphragm is at said initial position, and wherein said position sensing means further comprises:
    a second permanent magnet affixed to said valve head; and
    a second Hall effect sensor affixed to said body member so that said second sensor is triggered by said second magnet when said valve member is at said initial position.

12. The invention of claim 1 wherein said flexible diaphragm comprises a rolling diaphragm element.

13. A remote calibrator for a gas sensor having a sensing port for communication with the gas to be sensed comprising:
    first housing means having first and second ends, the first end for receiving the gas sensor port therein, said housing means having a plurality of openings formed therein proximate the first end for communicating ambient gas to the gas sensing port;
    diaphragm and valve assembly adapted to be received within the second end of the first housing, the assembly adapted so as to allow movement of a valve member from an open position wherein the ambient air is allowed to communicate with the gas sensing port, to a closed position wherein the flow of ambient gas to the port is substantially obstructed;
    the assembly further comprising a spring element cooperatively arranged with said diaphragm and said valve member to bias the valve member in the open position and a body member for supporting said diaphragm and said valve, said body member including means for constraining the movement of said valve along an axis extending toward the port of the gas sensing device;
    second housing means adapted to form with the diaphragm member a gas chamber, said second housing means being releasably secured to said second end of said first housing member;
    gas inlet means for communicating calibration gas into the gas chamber, the diaphragm and valve assembly being responsive to the calibration gas pressure in the chamber so as to drive the valve from the open position to the closed position as the gas pressure is increased to overcome the bias of said spring element; and
    a calibrated orifice provided through the diaphragm in communication with an opening formed through the valve so as to flood the gas sensing port with calibration gas when the valve is in the closed position.

14. A remote calibrator for a gas sensor having a sensing port for communication with the gas to be sensed, comprising:
    first housing means having first and second ends, the first end for receiving the gas sensor port therein, said housing means having a plurality of openings formed therein proximate the first end for communicating ambient gas to the gas sensing port;
    diaphragm and valve member assembly adapted to be received within the second end of the first housing, the assembly adapted so as to allow movement of said valve member from an open position wherein the ambient air is allowed to communicate with the gas sensing port, to a closed position wherein the flow of ambient gas to the port is substantially eliminated, said valve member comprising a valve head and a valve stem coupled thereto;
    the assembly further adapted to bias the valve member in the open position;
    second housing means adapted to form with the diaphragm member a gas chamber;
    gas inlet means for communicating calibration gas into the gas chamber, the diaphragm and valve assembly being responsive to the calibration gas pressure in the chamber so as to drive the valve member from the open position to the closed position as the gas pressure is increased; and
    a calibrated orifice provided through the diaphragm in communication with an opening formed through the valve so as to flood the gas sensing port with calibration gas when the valve member is in the closed position.

15. The remote calibrator of claim 14 further comprising sensing means adapted to provide an indication of the valve position.

16. The remote calibrator of claim 15 wherein the sensing means comprises Hall effect sensor means.

17. The remote calibrator of claim 14 wherein said diaphragm comprises a rolling diaphragm element.

18. The remote calibrator of claim 14 wherein said gas sensor is fitted within a recess in said first housing means at said first end thereof, and wherein said valve member further comprises dispersing means for dispersing the flow of gas from said valve member into said recess to achieve a more uniform gas distribution within said recess about the gas sensor.

19. The remote calibrator of claim 18 wherein said dispersing means comprises a gas deflector member disposed adjacent the opening formed in said valve head through which the gas flows, thereby dispersing the gas.

20. The remote calibrator of claim 19 wherein said gas deflector comprises a stem section which is received within said opening in said valve head and a deflector surface joined thereto, and wherein the gas flow through said opening tends to force the deflector surface away from said valve head.

21. The remote calibrator of claim 14 wherein said second housing means comprises a cap member threadingly engaging said second end of the first housing means.

22. The remote calibrator of claim 21 wherein said diaphragm and valve assembly further comprises a coil spring member cooperatively arranged to bias the valve member in the open position.

23. A remote calibrator for a gas sensor having a sensing port for communication with the gas to be sensed, comprising:

a housing structure having first and second ends, the first end for receiving the gas sensor port therein, said housing means having a plurality of openings formed therein proximate the first end for communicating ambient gas to the gas sensing port and having a shoulder surface extending within the structure intermediate said first and second ends thereof;

a cap member adapted to be removably secured to the housing structure at said second end thereof;

a diaphragm and valve assembly comprising a flexible diaphragm, a valve member and a body member for supporting said diaphragm means and said valve member, said assembly adapted to be received within said housing structure through said second end thereof, the valve member comprising a valve head and a valve stem, the assembly cooperatively arranged with said housing structure and said shoulder so as to allow movement of said valve member from an open position wherein said valve head is adjacent said body member and the ambient air is allowed to communicate with the gas sensing port, to a closed position wherein the valve head is adjacent said second end of said housing structure and the flow of ambient gas to the sensing port is substantially obstructed;

the diaphragm and valve assembly further comprising a diaphragm cup member received by said diaphragm, and coil spring having a first end engaging against said body member said shoulder adjacent said second end of the housing structure and a second end engaging against said diaphragm cup member so as to bias said valve member to the open position;

said diaphragm and said cap member adapted to form a gas chamber;

gas inlet means for communicating calibration gas into the gas chamber, the diaphragm and valve assembly being responsive to the calibration gas pressure in the chamber so as to drive the valve member from the open position to the closed position as the gas pressure is increased; and a calibrated orifice provided though the diaphragm in communication with a bore formed through said valve stem and head so as to flood the gas sensing port with calibration gas when the valve member is in the closed position.

24. The remote calibrator of claim 23 wherein said diaphragm comprises a rolling diaphragm element.

25. The remote calibrator of claim 23 further comprising position sensing means for providing a remote indication of the position of the valve member.

* * * * *